(12) United States Patent
Riccione et al.

(10) Patent No.: US 7,465,303 B2
(45) Date of Patent: Dec. 16, 2008

(54) EXTERNAL FIXATION ASSEMBLY

(75) Inventors: Nicholas Riccione, Slatington, PA (US); Shane M. Hollawell, Bayville, NJ (US); Thomas M. Rocchio, Breinigsville, PA (US)

(73) Assignee: Wright Medical Technology, Inc., Arlington, TN (US)

( * ) Notice: Subject to any disclaimer, the term of this patent is extended or adjusted under 35 U.S.C. 154(b) by 202 days.

(21) Appl. No.: 11/110,448

(22) Filed: Apr. 20, 2005

(65) Prior Publication Data

US 2005/0251135 A1    Nov. 10, 2005

Related U.S. Application Data (60) Provisional application No. 60/564,657, filed on Apr. 22, 2004, provisional application No. 60/621,437, filed on Oct. 22, 2004, now abandoned.

(51) Int. Cl.
*A61B 17/00* (2006.01)
*A61F 4/00* (2006.01)
*A61F 5/04* (2006.01)

(52) U.S. Cl. .............................. 606/54; 606/53; 606/55; 606/59

(58) Field of Classification Search .................. 606/54, 606/61, 53, 55, 59; 403/43–48; 16/360, 16/375–377
See application file for complete search history.

(56) References Cited

U.S. PATENT DOCUMENTS

| | | | | |
|---|---|---|---|---|
| 2,600,959 A | * | 6/1952 | Bender | 280/498 |
| 4,098,269 A | * | 7/1978 | Judet | 606/54 |
| 4,475,267 A | * | 10/1984 | Hathaway | 16/288 |
| 4,978,347 A | | 12/1990 | Ilizarov | |
| 4,978,348 A | * | 12/1990 | Ilizarov | 606/57 |
| 4,988,349 A | * | 1/1991 | Pennig | 606/58 |
| 5,067,954 A | | 11/1991 | Ilizarov | |
| 5,931,837 A | * | 8/1999 | Marsh et al. | 606/55 |
| 2006/0229604 A1 | * | 10/2006 | Olsen et al. | 606/54 |

* cited by examiner

*Primary Examiner*—Eduardo C Robert
*Assistant Examiner*—Andrew Yang
(74) *Attorney, Agent, or Firm*—Duane Morris LLP (57) ABSTRACT

An external fixation assembly for bone fusion is disclosed. The assembly includes an extension arm having a fixation joint portion and a pin element moveably disposed along the extension arm defining a first joint portion. The assembly further comprises a plurality of connecting pins for bone fusion. Each of the connecting pins is configured to engage with bone matter for bone fusion and to singly attach to one of the joint portions for support.

24 Claims, 12 Drawing Sheets

EXTERNAL FIXATION ASSEMBLY

CROSS-REFERENCE TO RELATED APPLICATIONS

This application claims the benefit of U.S. provisional application No. 60/564,657, filed Apr. 22, 2004, entitled "FOOT AND ANKLE EXTERNAL FIXATION SYSTEM," the entire contents of which are incorporated herein by reference.

This application also claims the benefit of U.S. Provisional Application No. 60/621,437, filed on Oct. 22, 2004 now abandoned, entitled "EXTERNAL RAIL FIXATION DEVICE FOR FUSIONS OF THE FOOT AND ANKLE," the entire contents of which are incorporated herein by reference.

BACKGROUND OF THE INVENTION

External fixation devices have been commonly used for various treatments of bone conditions. Such bone conditions include leg lengthening, osteotomies, arthrodesis, open fracture fixations, compound fracture fixations, and other bone conditions amenable to treatment by use of an external fixation modality. For example, external fixation devices are typically used in treatment of bones wherein frequent wound care is necessary to treat an open wound or a surgical site within an extremity. External fixation devices are also used in treatment of bones wherein conventional casting is not an option, e.g., treatment of fractures in the pelvis, the neck, the skull or other non-extremities of a patient.

Although current external fixation devices are adequate, many external fixation devices are relatively large and include numerous components, are complicated to use, surgically invasive, difficult to adjust, and involve challenging postoperative care and use. Thus, improvements may be made. For example, current external fixation devices involve relatively large and numerous components, creating operative difficulties to both the practitioner and postoperative difficulties to the patient. Many devices, for instance, involve a ring or "halo" member disposed about an affected area to provide support to pins for fixating bone matter. Such components, however effective, are relatively bulky and create difficulty for the physician to insert and for the patient to move independently.

These ring or halo fixation devices have been used by orthopedic surgeons and podiatrists in the treatment of some foot injuries and maladies. Some injuries or conditions involving the foot or ankle require that these devices be applied to the bones of the foot (e.g., calcaneus, tarsals, metatarsals, and phalanges) and the lower leg bones (e.g., tibia and fibula). In such circumstances, pins may be inserted into both the foot and lower leg bones in order to secure the fixation device. However, certain state laws in this country currently restrict podiatrists in their practice to performing manipulations and operative procedures on only the submalleolar region of a patient. Thus, devices requiring manipulations involving regions above the malleolar may be undesirable and/or inaccessible for use by podiatrists.

Thus, there is a need to provide an external fixation device that involves less components, is relatively easy to use, and may be used solely in the submalleolar region while maintaining effectiveness and providing relatively easy postoperative care.

BRIEF SUMMARY OF THE INVENTION

Embodiments of the present invention generally provide an external fixation assembly that involves less components and is relatively easy to use while maintaining effectiveness. Additionally, embodiments of the present invention provide relatively easy postoperative care and use to both the physician and the patient.

In one embodiment, the present invention provides an external fixation assembly for bone fusion. The assembly comprises a first extension arm and a second extension arm pivotally connected to the first extension arm at a fixation joint portion. The assembly further comprises a first attachment and a second attachment cooperable with the first attachment. The first attachment is moveably disposed on the first extension arm and has a first joint portion. The second attachment is moveably disposed on the second extension arm and has a second joint portion.

In this embodiment, the assembly further comprises a plurality of connecting pins for bone fusion. Each of the connecting pins has first and second ends. Each first end is configured to engage through bone matter for bone fusion and each second end is configured to attach to one of the joint portions for support. Each joint portion is configured to receive one of the connecting pins at a predetermined configuration for bone fusion of the bone matter.

In another embodiment, the present invention involves an assembly for bone fusion about a submalleolar region of a patient. The assembly comprises a first extension arm and a second extension arm cooperable with the first extension arm. The second extension arm is pivotally connected to the first extension arm at a fixation joint portion. The assembly further comprises a first pin element and a second pin element. The first pin element has a first joint portion and is moveably disposed along the first extension arm. The second pin element has a second joint portion and is moveably disposed along the second extension arm. The assembly further comprises a first brace member and a second brace member cooperable with the first brace member. The first brace member is attached to the first pin element at the first joint portion. The second brace member is attached to the second pin element at the second joint portion.

In this embodiment, the assembly further comprises a plurality of connecting pins for bone fusion about the submalleolar region. Each of the connecting pins has first and second ends. Each first end is configured to engage through bone matter and each second end is configured to attach to one of the joint portions for support. Each joint portion is configured to selectively receive one of the connecting pins having a predetermined configuration for bone fusion of the bone matter.

In yet another embodiment, the external fixation assembly comprises an extension arm having a fixation joint portion and a pin element moveably disposed along the extension arm defining a first joint portion. The assembly further comprises a plurality of connecting pins for bone fusion. Each of the connecting pins is configured to engage through bone matter for bone fusion and to singly attach to one of the joint portions for support.

In another aspect, the present invention provides a method of external fixation for bone fusion. The method comprises disposing a configuration of connecting pins through bone matter to be fused and engaging the configuration of connecting pins singly to joint portions of an external fixation assembly. The external fixation assembly includes an extension arm having a fixation joint and a pin element moveably disposed along the extension arm, defining a first joint portion. The configuration of connecting pins is disposed about the submalleolar region of the patient. The method further includes supporting the connecting pins and fusing the bone matter about the submalleolar region.

In yet another embodiment, the present invention provides a device for external fixation of a foot or ankle. In this aspect, the device comprises one or more extension arms, wherein each extension arm comprises a threaded rod and an affixed bone pin holding element rigidly affixed at one end of the threaded rod. The pin holding element includes an axial aperture. The device further comprises one or more moveable pin elements comprising a body portion comprising a bore through the length thereof wherein the bore is sized such that the moveable pin element is slidable on the threaded rod. The moveable one or more pin elements further comprise a pin holding element affixed to the body portion, wherein the pin holing element includes an axial aperture.

In this embodiment, the device further comprises a plurality of compression nuts, the threads of which are mateable with the threads of the threaded rod. When a compression nut is threaded onto the threaded rod and abuts a moveable pin element during use, the moveable pin element is prevented from sliding in the direction of the compression nut. In this embodiment, device optionally comprises one or more brace elements comprising an elongated substantially flat member. The member includes an axial aperture near one end thereof and a through-slot beginning near the opposing end and extending along the long axis of the brace element to near the aperture. The device further comprises one or more bolts and mating nuts, wherein the bolts comprise a threaded pin and a head portion, sized such that the pin is long enough to pass through the through-slots of two brace elements and is slideable along the through-slots, such that when the nut is threaded onto the bolt, the bolt and nut are able to form a compression lock holding the two brace elements rigidly. The device further comprises one or more collets comprising collet sleeves and collet nuts. The one or more collets are configured to hold a bone pin and to form a compression lock in the apertures when the collet nuts are tightened against the pin holding elements during use Further objects, features, and advantages of the present invention will become apparent from consideration of the following description and the appended claims when taken in connection with the accompanying drawings.

DETAILED DESCRIPTION OF THE INVENTION

The present invention generally provides an external fixation assembly that is relatively easy to use and provides simple postoperative care while maintaining effectiveness. Features of the embodiments provide an external fixation assembly for bone fusion preferably disposed lateral a submalleolar region of a patient. The assembly generally comprises first and second extension arms. The first and second extension arms cooperate together with brace members to receive connecting pins that are disposed through bone matter for bone fusion. The connecting pins are only laterally received by the extension arms at joint portions to provide support and stability to the pins, minimizing the area occupied by the assembly to allow for improved postoperative mobility to the patient.

Figure 1A:
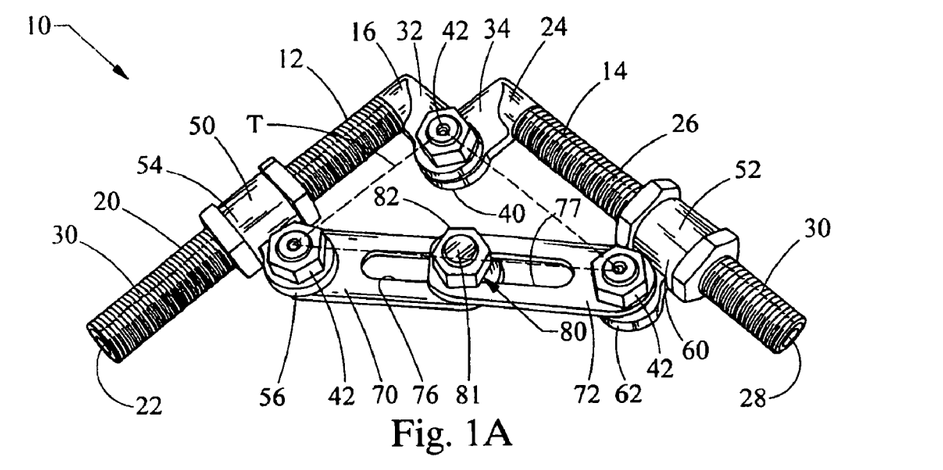
FIG. 1*a* is an elevated view of an external fixation assembly in one configuration in accordance with one embodiment of the present invention.
Figure 1B:
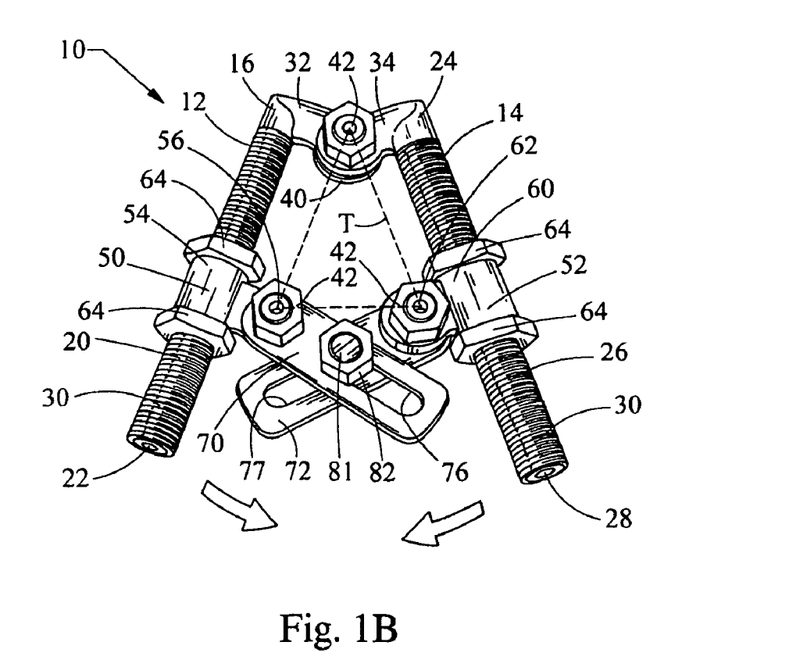
FIG. 1*b* is another elevated view of the external fixation assembly of FIG. 1*a*.

FIGS. 1*a* and 1*b* illustrate an external fixation assembly 10 for bone fusion preferably disposed laterally from a submalleolar region of a patient in accordance with one embodiment of the present invention. In this embodiment, the external fixation assembly 10 may be comprised of any suitable material such as stainless steel. As shown in FIGS. 1*a*-3, the external fixation assembly includes a first extension arm 12 and a second extension arm 14 cooperable with the first extension arm. The first extension arm 12 includes a first proximal end 16, a first threaded body 20 extending from the first proximal end, and a first distal end 22 opposite the proximal end. The second extension arm 14 has a second proximal end 24, a second threaded body 26 extending from the second proximal end, and a second distal end 28 opposite the second proximal end.

Each of the first and second threaded bodies 20 and 26 has outer threads 30 formed thereabout. In this embodiment, the outer threads 30 of each of the first and second threaded bodies 20 and 26 include about a ½ inch diameter. Preferably, each of the first and second extension arms 12 and 14 may include various sizes, e.g., 100 mm length long arm and 70 mm length short arm. Additionally, the first and second extension arms 12 and 14 are adjustable to take on various angular configurations dependent on the operative procedure. Thus, the external fixation assembly 10 may vary in size and shape.

Each of the first and second extension arms 12 and 14 includes a support head extending from its respective proximal end. As shown, a first support head 32 extends from the first proximal end 16 and has an aperture 33 formed therethrough. Similarly, a second support head 34 extends from the second proximal end 24 and has an aperture 35 formed therethrough. As shown, the first and second extension arms 12 and 14 are pivotally connected to each other by the support heads. In this embodiment, the first and second extension arms 12 and 14 are pivotally connected to each other at the respective apertures 33 and 35 of the support heads defining a fixation joint portion 40. As mentioned in greater detail below, the fixation joint portion 40 is configured to receive a connecting pin 84 to provide stability for bone fusion.

Figure 2:
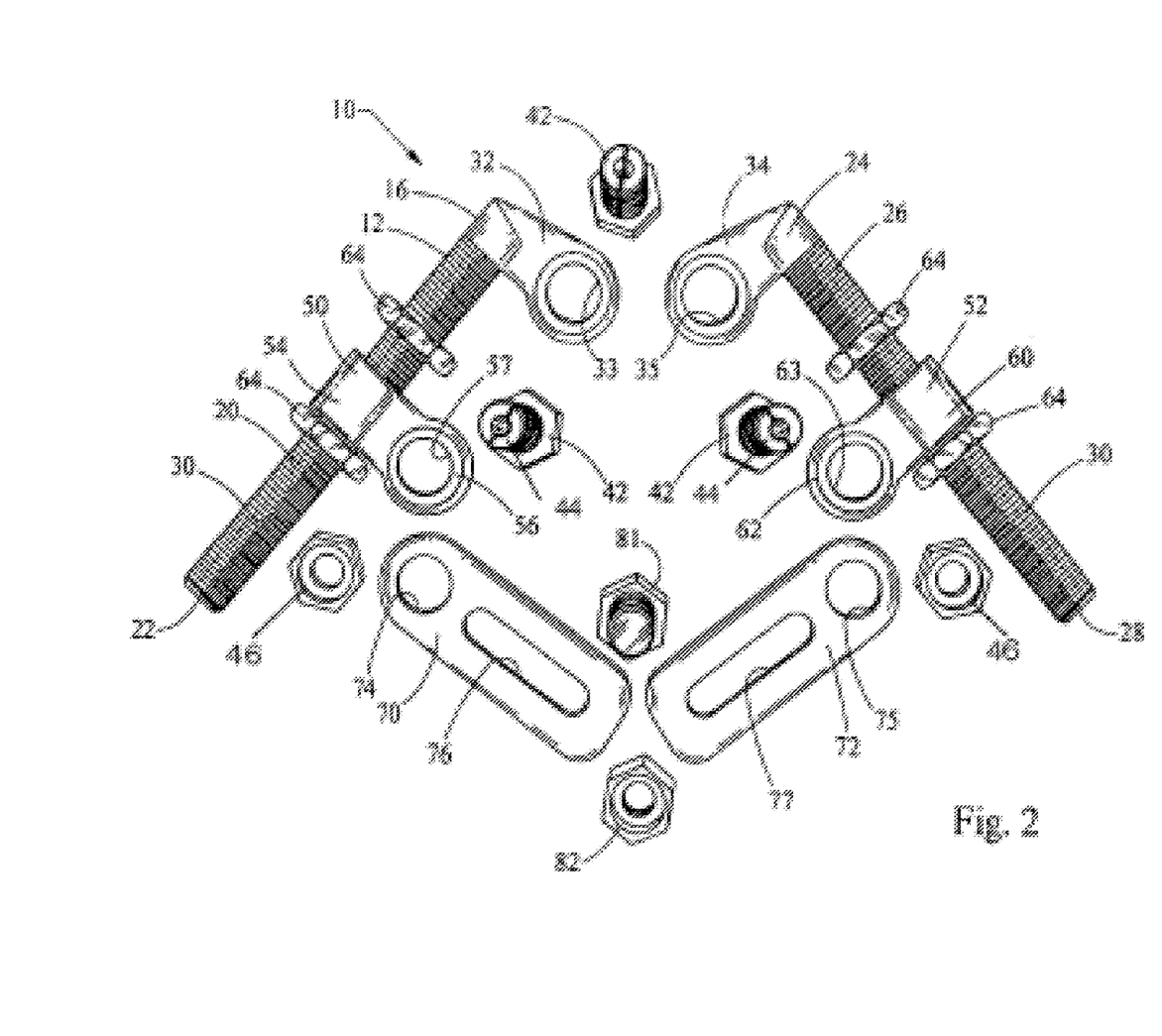
FIG. 2 is an exploded view of the external fixation assembly of FIG. 1*a*.
Figure 3:
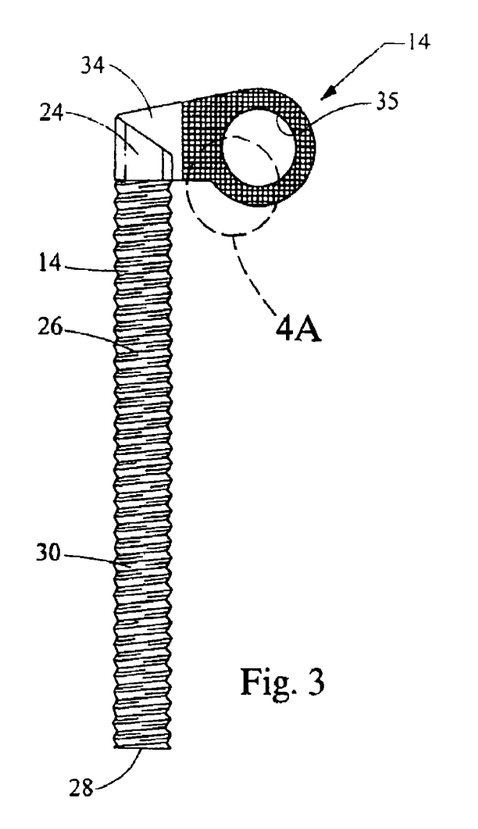
FIG. 3 is a side view of an extension arm of the external fixation assembly in accordance with one embodiment of the present invention.
Figure 4A:
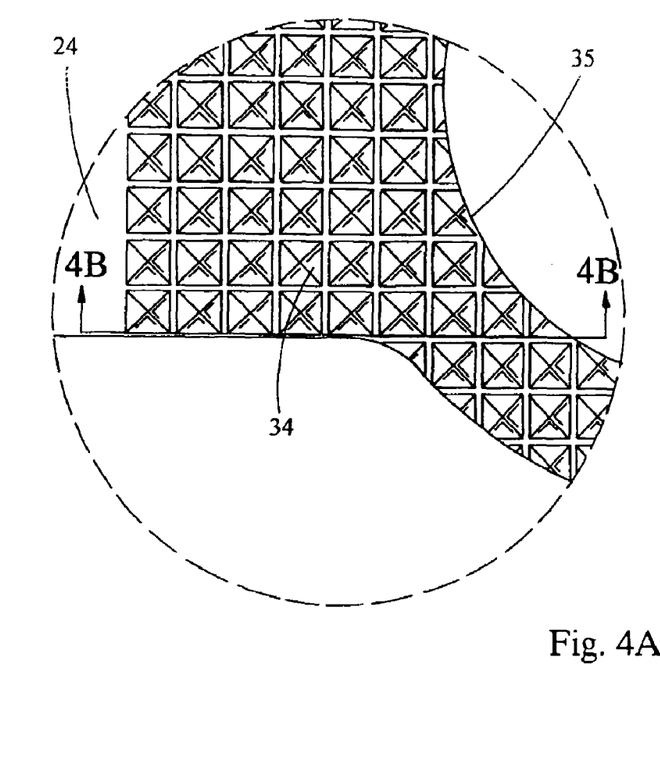
FIG. 4*a* is an enlarged view of the extension arm in circle 4*a* of FIG. 3.
Figure 4B:
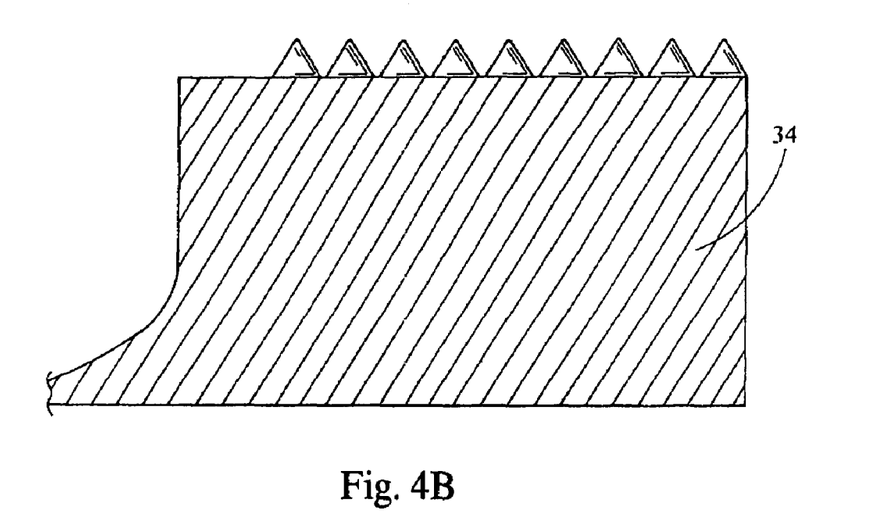
FIG. 4*b* is a cross-sectional view of the extension arm of FIG. 4*a* taken along line 4*b*-4*b*.

Preferably, the first and second extension arms 12 and 14 may be pivotally connected at the fixation joint portion by a pin clamp 42. In this embodiment, the pin clamp 42 includes a pin fastener 44 and a cooperating tightening nut 46. For example, the pin fastener 44 may be a 25-mm length drilled and slit threaded bolt with the tightening nut 46 cooperating therewith.

FIGS. 1A, 1B, and 2 further depict the external fixation assembly 10 including a first pin element 50 and a second pin element 52. The first pin element 50 has a first collar 54 formed about the first threaded body 20 and is moveably disposed along the first extension arm 12. A first joint portion 56 extends from the collar 54 and has an opening 57 formed therethrough. Similarly, the second pin element 52 has a second collar 60 formed about the second threaded body 26 and is moveably disposed along the second extension arm 14. A second joint portion 62 extends from the second collar 60 and has an opening 63 formed therethrough. As described in greater detail below, the first and second joint portions 56 and 62 receive connecting pins 84 to provide support to the assembly for bone fusion.

Each of the first and second pin elements 50 and 52 generally is configured to slide along the threaded body of its respective extension arm and is secured thereto using a pair of compression nuts 64. In this embodiment, a first set of 16-mm threaded hexagonal compression nuts 64 is matingly disposed about the first threaded body 20 to selectively lock the first pin element 50 along the first extension arm 12. Moreover, a second set of 16-mm threaded hexagonal compression nuts 64 is matingly disposed about the second threaded body 26 to selectively lock the second pin element 52 along the second extension arm 14.

Figure 5:
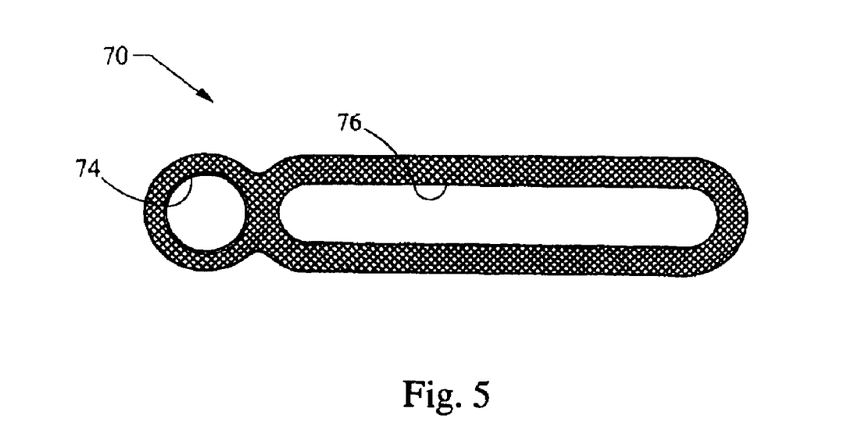
FIG. 5 is a side view of a brace member of the external fixation assembly in accordance with one embodiment of the present invention.
Figure 6A:
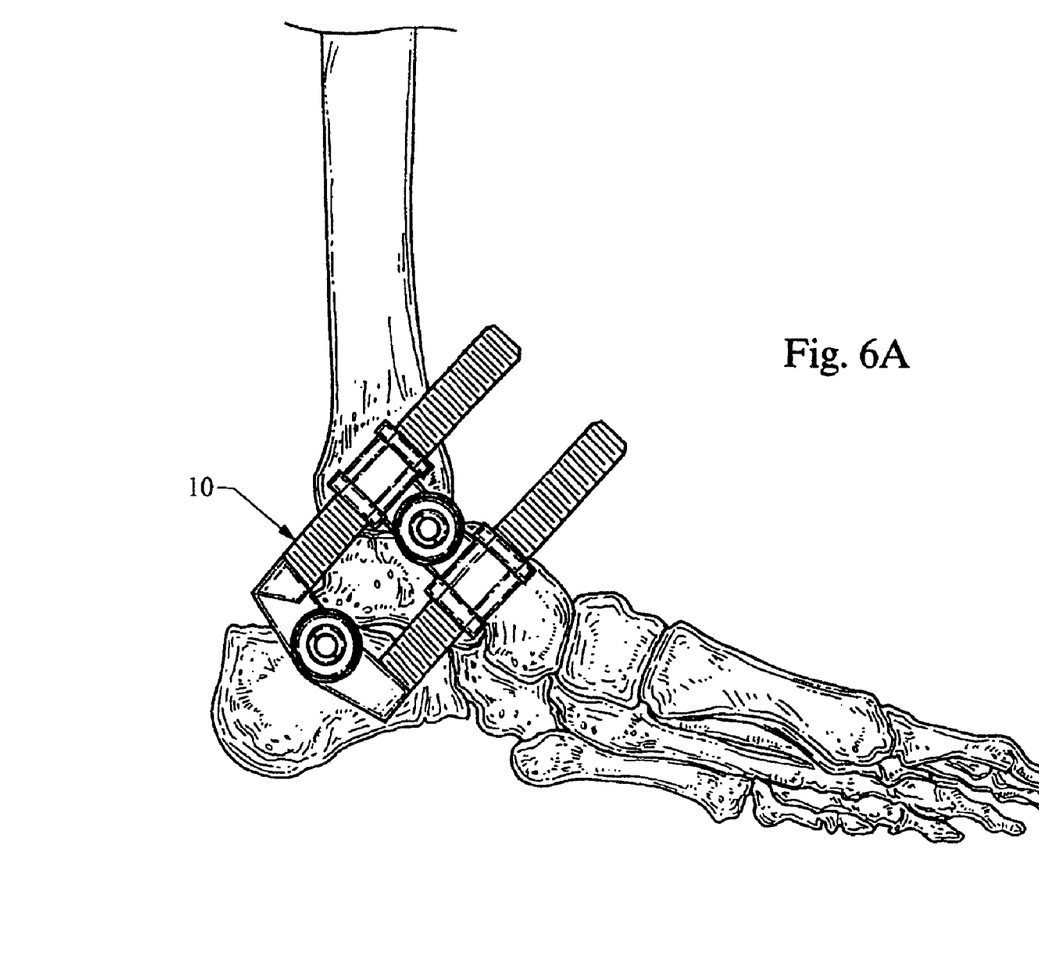
FIG. 6*a* is a subtalar fusion environmental view of the external fixation assembly.
Figure 6B:
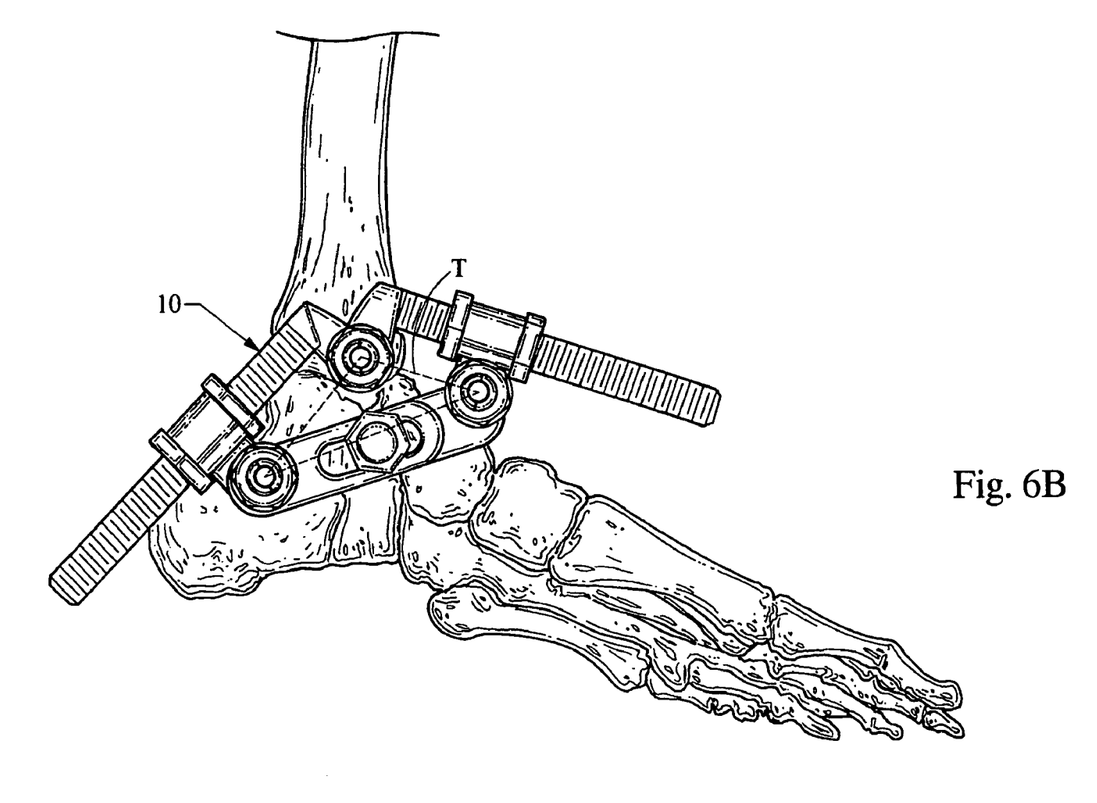
FIG. 6*b* is a triple arthrodesis environmental view of the external fixation assembly.
Figure 7A:
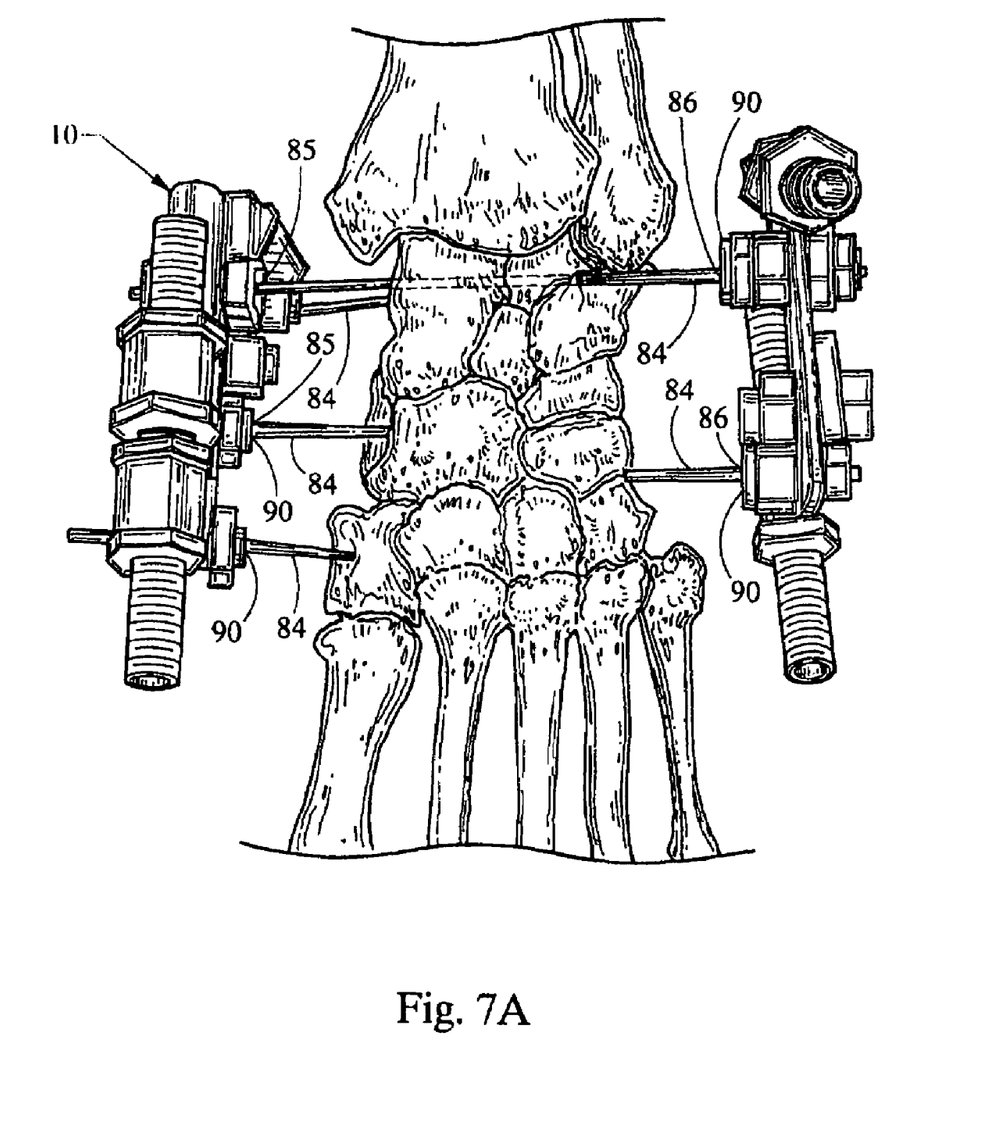
FIG. 7*a* is another triple arthrodesis environmental view of the external fixation assembly.
Figure 7B:
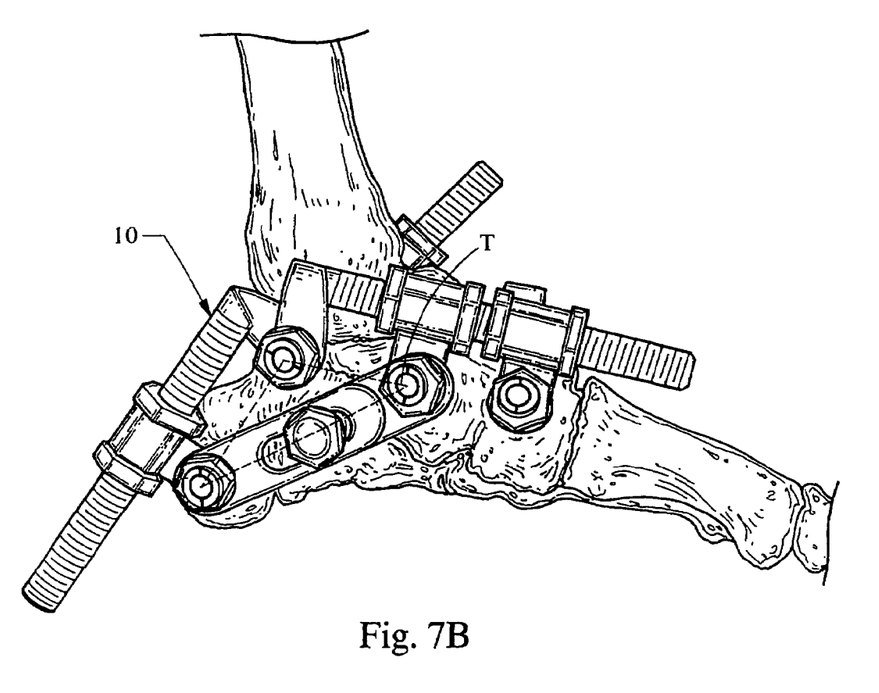
FIG. 7*b* is yet another triple arthrodesis environmental view of the external fixation assembly.

FIGS. 1a, 2, and 5 further illustrate a first brace member 70 and a second brace member 72 cooperable with the first brace member. The first brace member 70 is attached to the first pin element 50 at the first joint portion 56. The second brace member 72 is attached to the second pin element 52 at the second joint portion 62. In this embodiment, each brace member has a round hole 74, 75 formed therethrough for attachment to one of the pin elements 50, 52 and a slot 76, 77 preferably 9.5-mm wide. However, it is understood that parameters of the brace members may vary. For example, each of the brace members 70, 72 may take on a length of between about 35-mm and 75-mm.

As shown, the assembly 10 further comprises a brace fastener 80 for slidably attaching the first and second brace members 70, 72 together. In one embodiment, the two brace members 70, 72 may be adjusted and mated by a locking bolt 82, e.g., a 20-mm long ⅜-inch diameter round locking bolt and a locking nut 82, e.g., a 14-mm locking nut. In this embodiment, one of the surfaces of the brace member is smooth while the opposite surface is knurled to improve the mating strength of the brace members.

As shown in FIGS. 1a and 1b, the brace fastener 80 attaches the first and second brace members 70, 72, connecting the first and second extension arms 12, 14 together. As shown, the connection of the first and second extension arms 12, 14 defines a triangular shape T along the fixation joint portion 40, the first joint portion 56, and the second joint portion 62. As the brace fastener 80 may be disposed along slots 76 and 77, the shape T may be formed of various triangular shapes. It has been found that the connection of the first and second extension arms by the brace fastener, defining the triangular shape, provides added strength to the external fixation assembly of the present invention. In one embodiment, the connection by the brace fastener provides up to 50 percent added strength to the external fixation assembly.

FIGS. 6a-7b further depict a plurality of connecting pins 84 disposed at various locations and configurations for bone fusion preferably about the submalleolar region. As shown, each of the connecting pins 84 has first and second ends 85 and 86. Each of the connecting pins is configured to engage across bone matter. Moreover, each of the first and second ends 85, 86 of the pins is configured to attach to one embodiment of the external fixation assembly of the present invention. Additionally, each joint portion 40, 56, 62, defining triangular shape T, is configured to selectively receive one end of the connecting pins 84 having a predetermined configuration for bone fusion of the bone matter. The predetermined configuration is defined by the bone condition to be fused.

The connecting pins 84 may vary in size. For example, a "full pin" may have a 4-mm diameter, a 300-mm length with a self-drilling/self-tapping pin feature, and a 20-mm spiral drill tip length with a 5-mm diameter threads. A "half pin" may have a self-drilling/self-tapping 4-mm diameter 120-mm length, untapered with a trocar tip and 3.3-mm diameter threads. Thus, in this example, the pins 84 may be divided on long or short lengths based on the length of the threaded portions of the pins. Those skilled in the art will appreciate that many different types and sizes of pins can be employed without departing from the essential spirit and scope of the invention.

In this embodiment, the assembly further comprises a plurality of receiving members 90 for securing the second ends 86 of the connecting pins 84. Each of the joint portions 40, 56, 62 has one receiving member 90 disposed in its respective aperture to receive one of the second ends 86 to support the assembly 10 for bone fusion. As a result, support to the bone matter to be fused is enhanced.

In use, a pair of external fixation assemblies may be used, each laterally receiving one end of the connecting pins. Thus, the assemblies are preferably disposed laterally relative to the patient. The location and size of the assemblies provides minimal components for the physician to preoperatively handle and allows for enhanced postoperative mobility to the patient.

The external fixation assembly provides freedom of pin placement, ease of assembly, and stable fixation of bone fragments with the possibility of axial loading of the lower extremity and immediate range of motion of all adjacent joints. Bone conditions that may apply may include triple arthrodesis (see FIGS. 6b-7a), subtular arthrodesis (see FIG. 6a), ankle arthrodesis, and stable fixation of fractures of foot bones.

Figure 8:
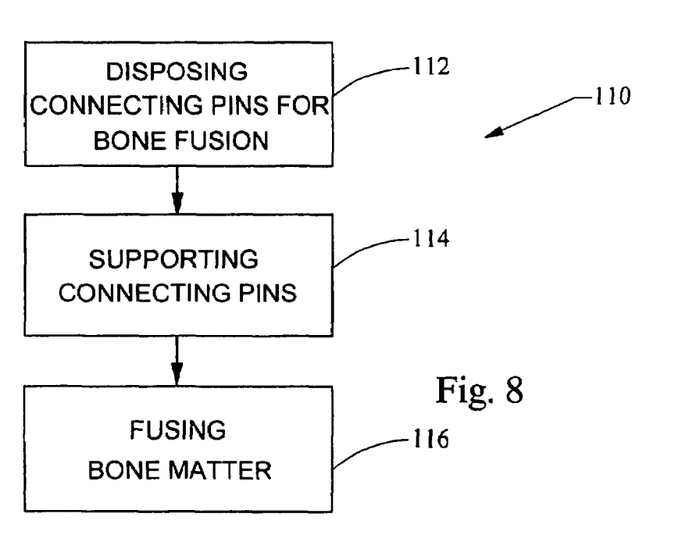
FIG. 8 is a flowchart of one method of external fixation for bone fusion.
Figure 9A:
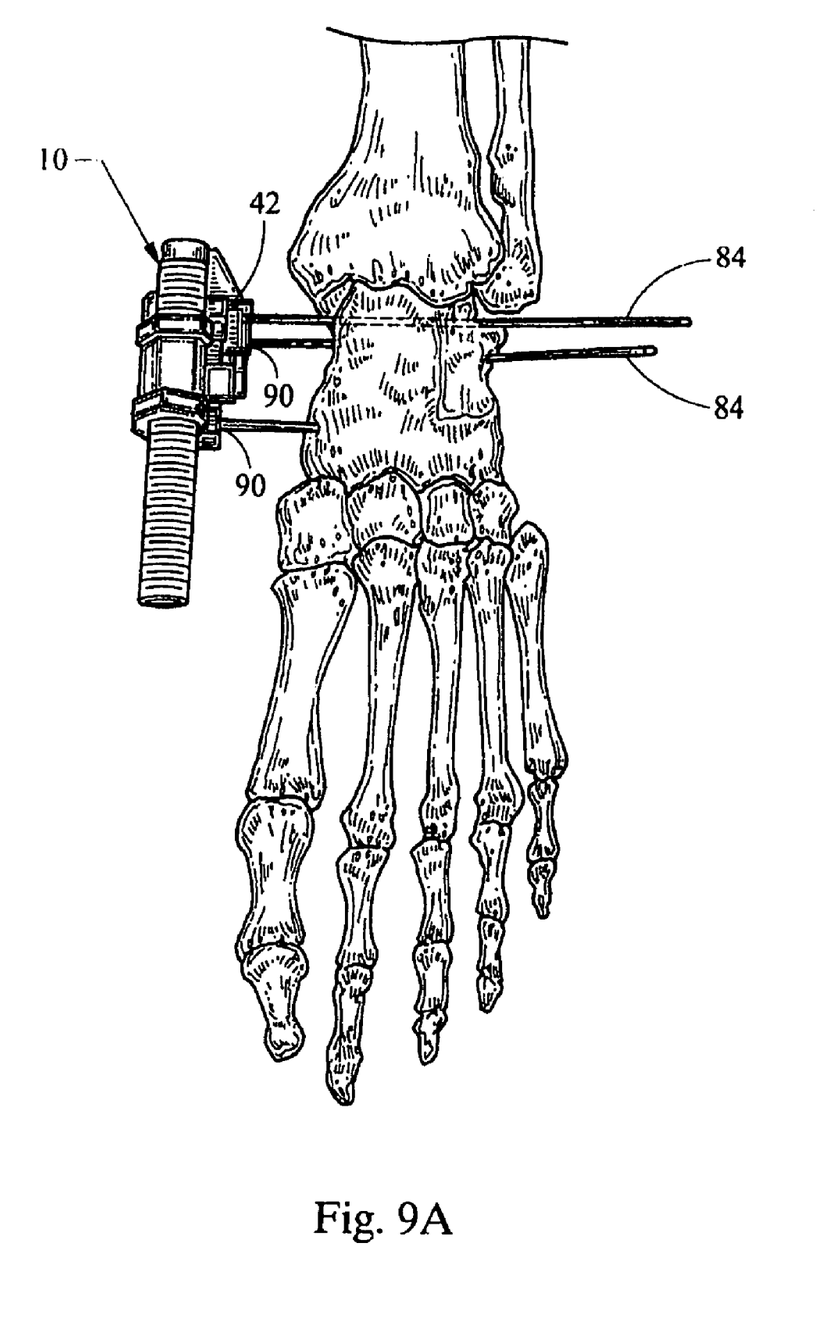
FIG. 9*a* is an anterior view of a submalleolar placement of the external fixation assembly for a triple arthrodesis.
Figure 9B:
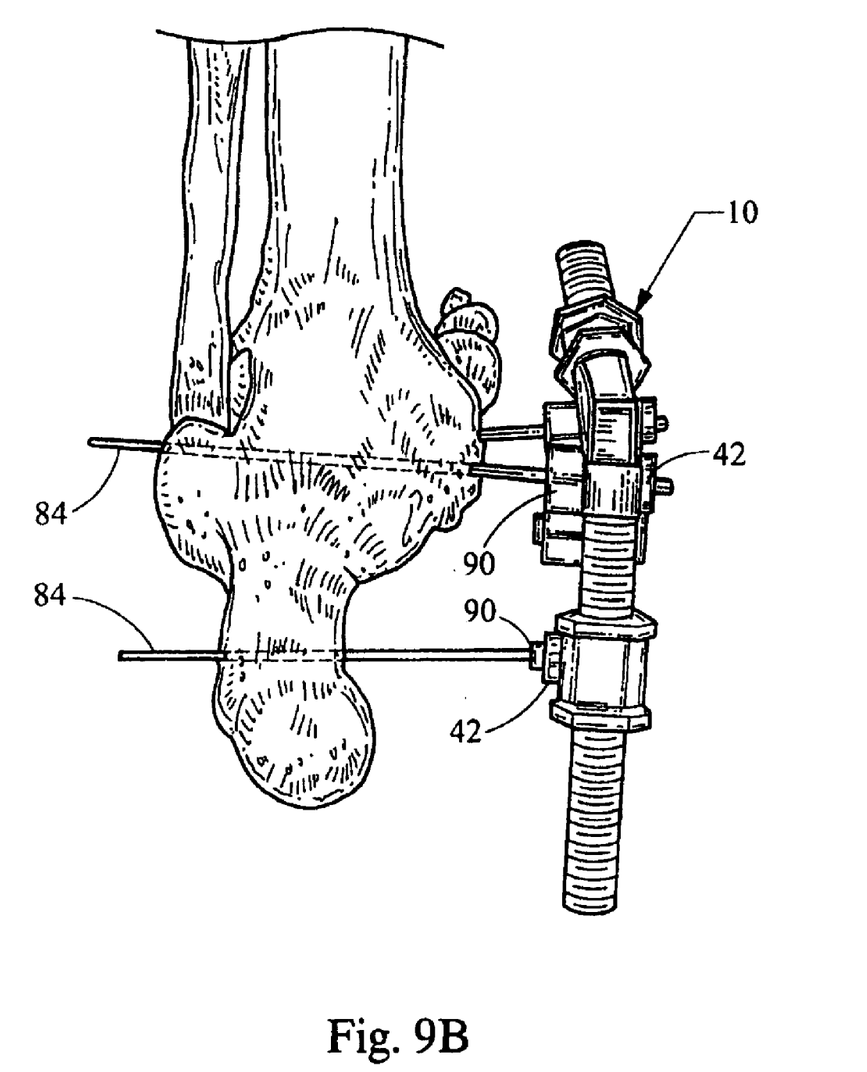
FIG. 9*b* is a posterior view of the submalleolar placement of the external fixation assembly in FIG. 9*a* for a triple arthrodesis.
Figure 10A:
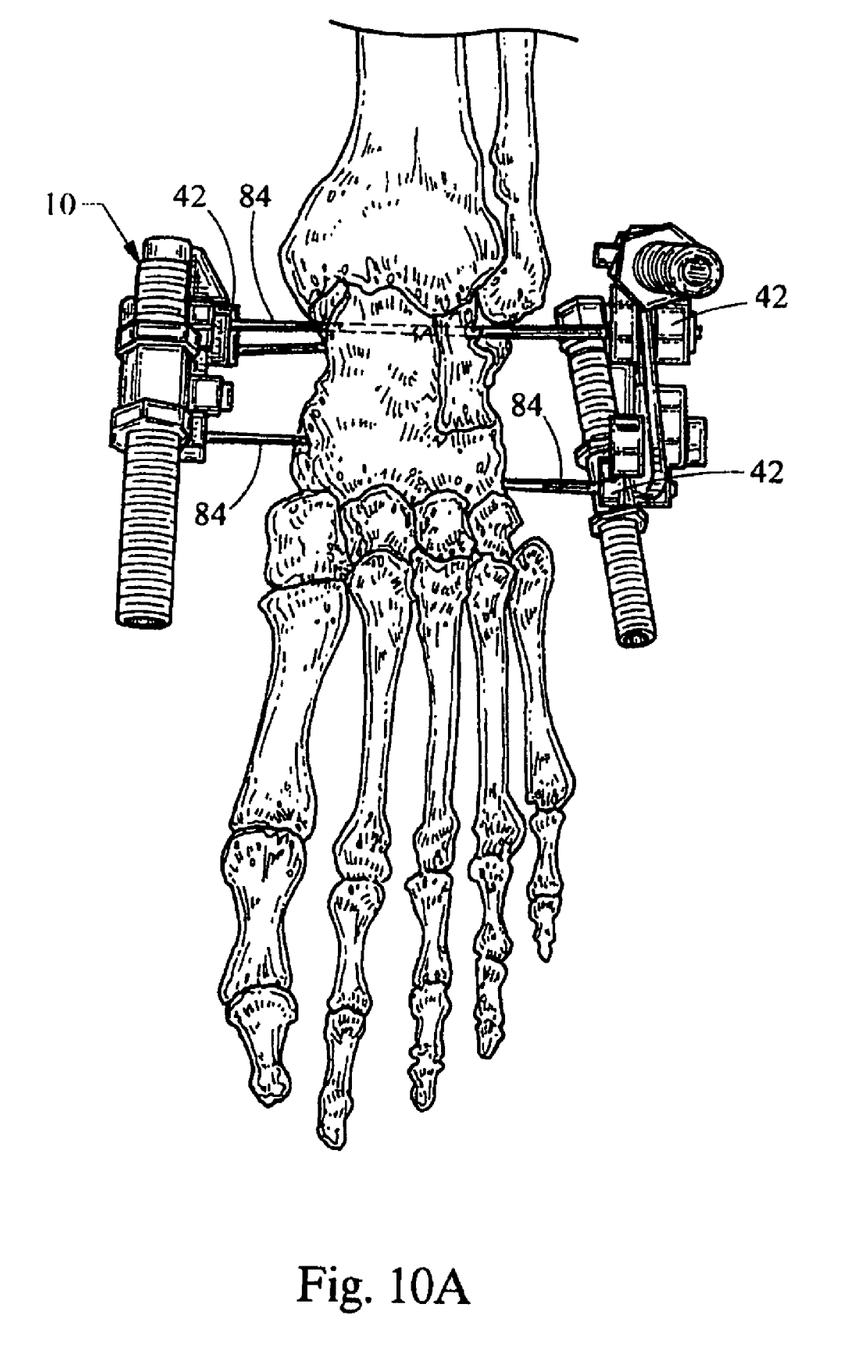
FIG. 10*a* is another anterior view of the submalleolar placement of the external fixation assembly for a triple arthrodesis.
Figure 10B:
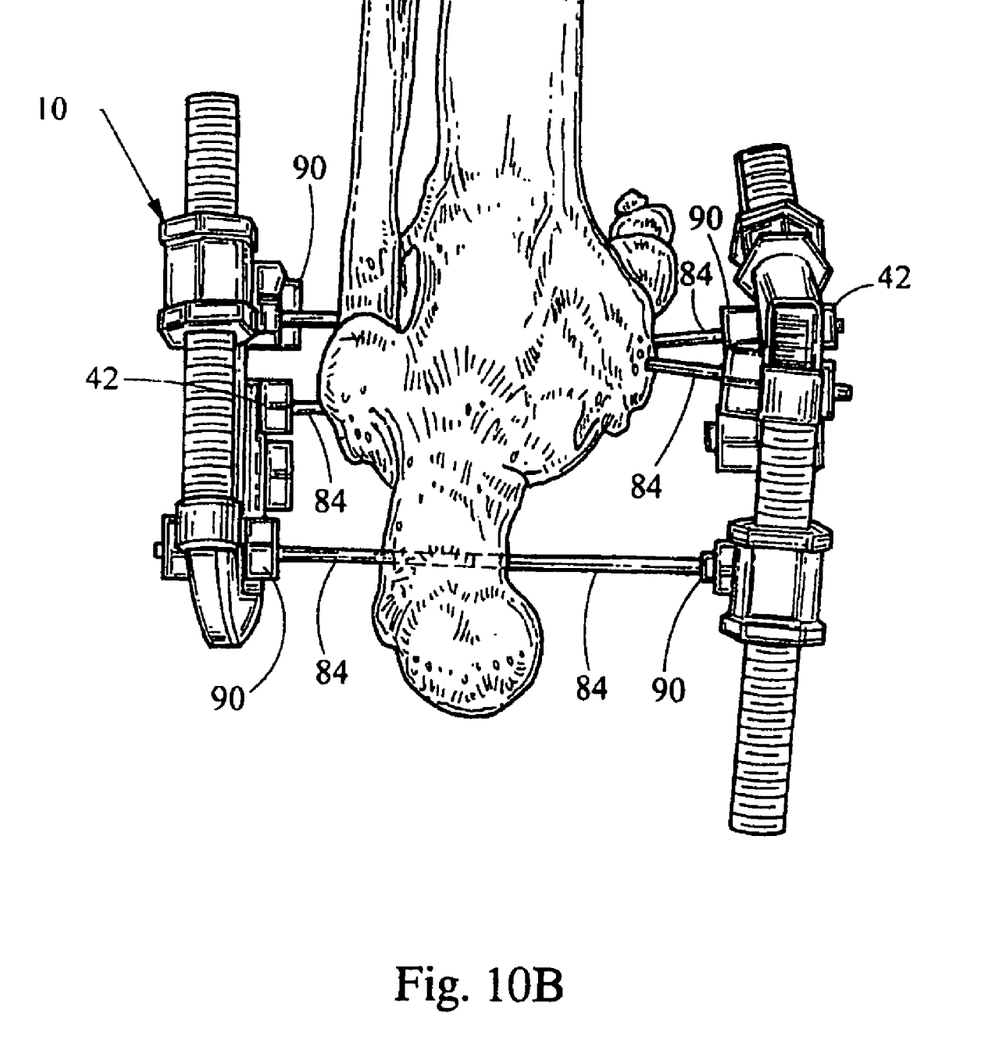
FIG. 10*b* is another posterior view of the submalleolar placement of the external fixation assembly in FIG. 10*a* for a triple arthrodesis.

FIG. 8 illustrates a method 110 or surgical procedure of applying an external fixation on a patient for bone fusion. Preoperatively, the patient is placed supine on an X-ray lucent table with a sandbag under the ipsilateral buttock. Either general or regional anesthesia may be used. The lower limb is preferably prepared and draped in such a way that the ankle may be manipulated relatively freely. A tourniquer may be used as desired.

An arthrodesis site is then prepared. Thus, joint surfaces of the patient are resected, aligned, and bone grafted (if needed) to establish a stable plantigrade foot position. Percutaneous fixation of the arthrodesis sites is preferred to maintain alignment. Prior to percutaneous pin application, the skin and soft tissue structures are distributed so incision margins can be reapproximated without tension. Fluoroscopy may be used to confirm alignment.

Insertion of a connecting pin, e.g., a center threaded transfixion pin, may then be inserted. Pre-drilling may be performed. In this example of a center threaded transfixion pin insertion, the center threaded transfixion pin may have a drill at its tip. A 0.5 cm drill tip may be used and a blunt dissection is continued down to bone.

As shown, the method 110 comprises disposing in box 112 a plurality of connecting pins through bone matter of a patient for bone fusion preferably across the sub-malleolar region of the patient. The inserted connecting pins are preferably positioned perpendicular to the long axis of the rear foot and parallel to the weight-bearing surface. One pair or more of pins may be used, e.g., half pins and center threaded transfixion pins. The first pin positioned is preferably a calcaneal connecting pin applied across the calcaneal. An attempt is preferably made to position subsequent pins parallel to the calcaneal pin in all planes.

In order to reduce the opportunity for skin traction during ambulation, the foot is preferably dorsiflexed during calcaneal pin insertion and plantarflexed during a talar pin insertion, a navicular pin inserstion, and cuboid pin insertion.

In inserting a connecting pin, a trocar and soft tissue guide are preferably first inserted to establish pin orientation. A determination is conducted to confirm the position is perpendicular to the long axis of the rear foot and parallel to the weight-bearing surface. Once the pin orientation is confirmed, the trocar is removed and the soft tissue guide is tapped with a mallet to seat it into the bone. The center threaded transfixion pin exits out of the skin at a second site. After penetration of the far cortex, the skin is then tented with the tip of the pin. The skin is then pre-cut prior to advancement of the pin. The threads of the pin are centered within the body of the bone being penetrated.

For half pin insertion, the following technique is preferred. A small stab incision is made at the desired site of insertions. A blunt dissection down to bone is performed using a hemostat. After pin orientation is confirmed, the pin is drilled into the bone. Final positioning can be performed under fluoroscopy with a bone screw T-wrench as known in the art. Half pins are preferably bi-cortical with about two threads or two millimeters protruding from the far cortex. Image intensification may be used to confirm depth of penetration. The bone screw T-wrench is used to slowly advance the half pin into bone.

The method 110 further includes supporting in box 114 the plurality of connecting pins with an extension arm having a fixation joint portion and a pin element moveably disposed along the extension arm to define a first joint portion. Each of the assemblies receiving connecting pins maintains support to the connecting pins for bone fusion.

The method 110 preferably further includes fusing in box 116 the bone matter about the submalleolar region of the patient. The pin clamps 42 are securely fixed to the pins with a pin wrench. Compression across the fusion sites is obtained by appropriately rotating the nuts adjacent to the pin clamps 42 after the clamps have been secured to the pins. The fluoroscope is used to confirm apposition of bone surfaces. The frame preferably does not extend beyond the plantar skin with weight bearing. The frame preferably does not extend posterior to the heel.

An example of triple arthrodesis surgical insertions (FIGS. 9a-10b) of various connecting pins 84 is now described below. The calcaneal connecting pin 84 through the calcaneus may be inserted from medial to lateral, positioned in the posterior inferior aspect of the calcaneus. This direction of insertion allows for avoidance of the medical neurovascular bundle. A preoperative identification and marking of the posterior tibial artery assists in avoiding the medial neurovascular bundle. The calcaneal connecting pin 84 is preferably placed perpendicular to the long axis of the rear foot and parallel to the weight-bearing surface. In this example, it is understood that the calcaneal connecting pin 84 placement does not allow the frame to extend beyond the plantar skin with weight bearing.

A center threaded transfixion pin 84 is preferably used for fixation of the calcaneus. The center threaded transfixion pin 84 allows for medial and lateral calcaneal frame application for stabilization of the subtalar joint and also allows for calcaneocuboid compression.

The talar connecting pin 84 through the talus is inserted from medial to lateral, positioned in the neck of the talus. The skin and soft tissue structures are positioned toward the incision line prior to talar pin insertion. This allows the skin to be closed without tension after pin placement. The skin is then tensioned, and a 1 cm incision with dissection down to bone is performed. The soft tissue guide is applied and the talar pin 84 is inserted as described above. Prior to inserting the pin 84, with the pin tip pressed against the bone, the foot is maximally dorsiflexed. This maneuver will identify if the pin position will impinge against the medial malleolus during ambulation. If no abutment occurs, pin insertion may proceed with a center threaded transfixion pin 84. The center threaded transfixion pin allows for medial and lateral talar frame application for stabilization of the subtalar joint and also allows for the talonavicular compression.

Skin closure prior to assembly application is preferred. The external fixation assembly is then positioned over talar and calcaneal pins from the medial site of the foot first. The fixation joint portion 40 is positioned over to receive the talar pin 84 via the receiving members 90 with the extension arms 12, 14 extending down towards bottom of the foot. The assembly is preferably applied so the pin clamps 42 have about a 1 cm clearance from the foot skin after final tightening. Pin clamps 42 accommodate the connecting pins inserted at different angles in both the transverse and frontal plains. A distal clamp is positioned over the insertion point into the navicular bone and the nuts are finger tightened.

The navicular connecting pin 84 through the navicular is inserted from medial to lateral, positioned in the center of the navicular. The distal clamp of the fixator is used as a guide. The skin and soft tissues are tensioned as was performed for the talar pin 84 insertion above. In this example, a 3 mm-thread half pin is used and the half pin is initially drilled to 5-6 mm of depth. The bone screw T-wrench is used to advance the half pin deeper. Image intensification may be used to avoid over penetration. Two threads or two millimeters of the pin should extend beyond the lateral cortex of the navicular.

It is to be understood that the surgeon may elect to place a cuneiform connecting pin 84 through the cuneiforms in lieu of a navicular connecting pin. In this example, a half pin is inserted from medial to lateral. The skin and soft tissues are tensioned toward the incision line prior to pre-drilling. In this example, a 33 mm-thread half pin is used. With the skin tensioned, the insertion technique as previously described for half pins is performed. The bone screw T-wrench is used to farther insert the half pin. Image intensification is used to avoid over penetration. Two threads or two millimeters of the pin preferably extend beyond the lateral cortex of the lateral cuneiform. Additional clamp with the original clamp is used for the cuneiform pin. All the connectors of the medial part of the fixator are finger tightened after additional check for alignment and positioning.

The assembly is then positioned over the calcaneal and talar pins 84 from the lateral side of the foot. The fixation joint portion 40 is positioned to receive the calcaneal pin 84 via the receiving member 90 with the extension arms 12, 14 extending towards the front of the foot. The assembly is preferably applied so the pin clamps 42 have approximately 1 cm clearance from the foot skin after final tightening. The pin clamps 42 accommodate pins inserted at different angles in both the transverse and frontal plains. A distal bottom clamp should be positioned over the insertion point into the cuboid bone and all the nuts are finger tightened.

The pin 84 through the cuboid is inserted from lateral to medial, positioned in the center of the cuboid. The lower-distal clamp of the fixator is used as a guide. A 3 mm-thread half pin may be used. With the skin tensioned, the insertion technique as previously described for half pins is performed. The bone screw T-wrench is used to advance the half pin. Image intensification is used to avoid over penetration. Two threads or two millimeters of the pin preferably extend beyond the medial cortex of the cuboid. The half pin in may be advanced farther into the navicular bone for the increased stability of the frame.

Additional pins can be used at the surgeon's discretion. Additional pins may be added proximal to the talonavicular and calcaneocuboid arthrodesis sites.

The external fixation assembly 10 for triple arthrodesis allows fast application of the frame, freedom of the pin placement for simultaneous stabilization of the arthrodesis sites, immediate range of motion of the ankle joint (if ankle fixation is not chosen for additional stability) and permits axial loading of the lower extremity.

Postoperatively, incision sites are dressed in routine sterile fashion. For example, sterile gauze is placed around all pins to prevent pistoning of the soft tissue on the pins. Pin sites are subsequently monitored.

While the present invention has been described in terms of preferred embodiments, it will be understood, of course, that the invention is not limited thereto since modifications may be made to those skilled in the art, particularly in light of the foregoing teachings.

The invention claimed is:

1. An external fixation assembly for bone fusion, the assembly comprising:
   a first extension arm and a second extension arm pivotally connected to the first extension arm at a fixation joint portion, wherein the first extension arm includes a first threaded body having outer threads formed thereabout and the second extension arm includes a second threaded body having outer threads formed thereabout, and further wherein said fixation joint portion defines a single pivot axis;
   a first attachment collar and a second attachment collar cooperable with the first attachment collar, the first attachment collar being moveably disposed on the first extension arm and having a first joint portion, the second attachment collar being moveably disposed on the second extension arm and having a second joint portion wherein said first joint portion and said second joint portion each defines a single pivot axis, and said first attachment collar and said second attachment collar further include:
   a first pin element and a second pin element, the first pin element being moveably disposed along the first extension arm and the second pin element being moveably disposed along the second extension arm; and
   a first brace member and a second brace member cooperable with the first brace member, the first brace member being attached to the first pin element at the first joint portion, the second brace member being attached to the second pin element at the second joint portion; and
   a plurality of connecting pins for bone fusion, each of the connecting pins having first and second ends, each first end being configured to engage through bone matter for bone fusion, each second end being configured to attach to one of said fixation joint portion, said first and said second joint portions for support, each of said fixation joint portion, said first and said second joint portions being configured to receive one of the connecting pins in coaxial relation to said single pivot axis of said joint portion, and at a predetermined configuration for bone fusion of the bone matter, and further comprising a plurality of receiving members for securing the second ends of the connecting pins, each of the joint portions having one receiving member disposed therein to receive one second end to support the assembly for bone fusion, and a brace fastener for attaching the first and second brace members together, defining a triangular shape along the fixation joint portion, the first joint portion, and the second joint portion.

2. The assembly of claim 1 further comprising:
   a first set of threaded compression nuts matingly disposed about the first threaded body to selectively lock the first pin element along the first extension arm; and
   a second set of threaded compression nuts matingly disposed about the second threaded body to selectively lock the second pin element along the second extension arm.

3. The assembly of claim 1 wherein the predetermined configuration is defined by the bone matter for fusion.

4. The assembly of claim 1 wherein each of the first and second extension arms has a proximal end and a distal end, the first and second extension arms being pivotally connected at the proximal ends.

5. An external fixation assembly for bone fusion about a submalleolar region of a patient, the assembly comprising:
   a first extension arm and a second extension arm cooperable with the first extension arm, the second extension arm being pivotally connected to the first extension arm at a fixation joint portion, wherein the first extension arm includes a first threaded body having outer threads formed thereabout and the second extension arm includes a second threaded body having outer threads formed thereabout, a first pin element having a first collar formed about the first extension arm, a second pin element having a second collar formed about the second extension arm, and further wherein said fixation joint portion includes a pin clamp having a longitudinally extending bore that defines a single pivot axis about which said first extension arm and said second extension arm cooperate;
   wherein, the first pin element has a first joint portion and being moveably disposed along the first extension arm, and the second pin element has a second joint portion and being moveably disposed along the second extension arm, wherein said first joint portion and said second joint portion each includes a pin clamp having a longitudinally extending bore that defines a pivot axis, and;
   a first brace member and a second brace member cooperable with the first brace member, the first brace member being attached to the first pin element at the first joint portion, the second brace member being attached to the second pin element at the second joint portion, and further comprising a brace fastener for attaching the first and second brace members together, defining a triangular shape along the fixation joint portion, the first joint portion, and the second joint portion; and a plurality of connecting pins for bone fusion about the submalleolar region, each of the connecting pins having first and second ends, each first end being configured to engage with bone matter and each second end being configured to attach to one of said fixation joint portion, said first and said second joint portions for support, each joint portion being configured to selectively receive one of the connecting pins within said longitudinally extending bore of said pin clamp, and having a predetermined configuration for bone fusion of the bone matter.

6. The assembly of claim 5 further comprising:
a first set of threaded compression nuts matingly disposed about the first threaded body to selectively lock the first pin element along the first extension arm;
a second set of threaded compression nuts matingly disposed about the second threaded body to selectively lock the second pin element along the second extension arm.

7. The assembly of claim 5 further comprising:
a plurality of receiving members for securing the second ends of the connecting pins, each of the joint portions having one receiving member disposed therein to receive one second end to support the assembly for bone fusion.

8. The assembly of claim 5 wherein the predetermined configuration is defined by the bone matter for fusion.

9. The assembly of claim 5 wherein each of the first and second extension arms has a proximal end and a distal end, the first and second extension arms being pivotally connected at the proximal ends.

10. An external fixation assembly for bone fusion, the assembly comprising:
a first extension arm having a fixation joint portion having a pin clamp with a longitudinally extending bore that defines a single pivot axis; and a second extension arm cooperable with the first extension arm, the second extension arm being pivotally connected to the first extension arm at the fixation joint portion so as to pivot about said single pivot axis;
a first pin element moveably disposed along the extension arm defining a first joint portion and a second pin element, the second pin element having a second joint portion and being moveably disposed along the second extension arm; wherein the first extension arm includes a first threaded body having outer threads formed thereabout and the second extension arm includes a second threaded body having outer threads formed thereabout, the first pin element having a first collar formed about the first extension arm, the second pin element having a second collar formed about the second extension arm;
a first brace member and a second brace member cooperable with the first brace member, the first brace member being attached to the first pin element at the first joint portion, the second brace member being attached to the second pin element at the second joint portion; and further comprising a first set of threaded compression nuts matingly disposed about the first threaded body to selectively lock the first pin element along the first extension arm; and a second set of threaded compression nuts matingly disposed about the second threaded body to selectively lock the second pin element along the second extension arm; and a plurality of connecting pins for bone fusion, each of the connecting pins being configured to engage with bone matter for bone fusion and to singly attach to one of the joint portions for support.

11. The assembly of claim 10 further comprising:
a plurality of receiving members for securing the second ends of the connecting pins, each of the joint portions having one receiving member disposed therein to receive one second end to support the assembly for bone fusion.

12. The assembly of claim 10 further comprising a brace fastener for attaching the first and second brace members together, defining a triangular shape along the fixation joint portion, the first joint portion, and the second joint portion.

13. The assembly of claim 10 wherein each of the first and second extension arms has a proximal end and a distal end, the first and second extension arms being pivotally connected at the proximal ends.

14. The assembly of claim 10 wherein each of the connecting pins has first and second ends, each first end being configured to engage with bone matter for bone fusion and each second end being configured to singly attach to one of the joint portions for support, each joint portion being configured to selectively receive one of the connecting pins at a predetermined configuration for bone fusion of the bone matter.

15. The assembly of claim 14 wherein the predetermined configuration is defined by the bone matter for fusion.

16. A method of external fixation for bone fusion, the method comprising:
disposing a plurality of connecting pins through bone matter of a patient for bone fusion about the submalleolar region of the patient; and
supporting the plurality of connecting pins with a first extension arm and a second extension arm each having a fixation joint portion that defines a single pivot axis about which said first extension arm and said second extension arm cooperate and a pin element moveably disposed along each extension arm to define a first joint portion and a second joint portion, wherein the first extension arm includes a first threaded body having outer threads formed thereabout and the second extension arm includes a second threaded body having outer threads formed thereabout, the first pin element having a first collar formed about the first extension arm, the second pin element having a second collar formed about the second extension arm;
attaching a first end of a first brace member to a first end of said first extension arm;
attaching a first end of a second brace member to a first end of said second extension; and
attaching a second end of said first brace to a second end of said second brace so as to thereby define a triangular shape along the fixation joint portion, the first joint portion, and the second joint portion.

17. The method of claim 16 wherein the assembly further comprises:
a first set of threaded compression nuts matingly disposed about the first threaded body to selectively lock the first pin element along the first extension arm; and
a second set of threaded compression nuts matingly disposed about the second threaded body to selectively lock the second pin element along the second extension arm.

18. The method of claim 16 further comprising:
a plurality of receiving members for securing the second ends of the connecting pins, each of the joint portions having one receiving member disposed therein to receive one second end to support the assembly for bone fusion.

19. The method of claim 16 wherein the assembly further comprises a brace fastener for attaching the first and second brace members together, so as to thereby define said triangular shape along the fixation joint portion, the first joint portion, and the second joint portion.

20. The method of claim 16 wherein each of the first and second extension arms has a proximal end and a distal end, the first and second extension arms being pivotally connected at the proximal ends.

21. The method of claim 16 wherein each of the connecting pins has first and second ends, each first end being configured to engage with bone matter for bone fusion and each second end being configured to singly attach to one of the joint portions for support, each joint portion being configured to selectively receive one of the connecting pins at a predetermined configuration for bone fusion of the bone matter.

22. The method of claim 21 wherein the predetermined configuration is defined by the bone matter for fusion.

23. The method of claim 21 further comprising fusing the bone matter about the submalleolar region of the patient.

24. An external fixation assembly for bone fusion, the assembly comprising:
- a first threaded extension arm and a second threaded extension arm pivotally connected to the first threaded extension arm at a fixation joint portion having a pin clamp with a longitudinally extending bore that defines a single pivot axis about which said first extension arm and said second extension arm pivot;
- a first collar and a second collar cooperable with the first collar, the first collar being moveably disposed on the first threaded extension arm and having a first joint portion, the second collar being moveably disposed on the second threaded extension arm and having a second joint portion wherein said first collar is moveably disposed along said first threaded extension arm and said second collar is moveably disposed along said second threaded extension arm; and further including a first brace member and a second brace member cooperable with said first brace member, said first brace member being attached to the first collar at the first joint portion, the second brace member being attached to the second collar at the second joint portion; and
- a plurality of connecting pins for bone fusion, each of the connecting pins having first and second ends, each first end being configured to engage through bone matter for bone fusion, each second end being configured to attach to one of the joint portions for support, each joint portion being configured to receive one of the connecting pins at a predetermined configuration for bone fusion of the bone matter, and further comprising a plurality of receiving members for securing the second ends of the connecting pins, each of the joint portions having one receiving member disposed therein to receive one second end to support the assembly for bone fusion, and a brace fastener for attaching the first and second brace members together, defining a triangular shape along the fixation joint portion, the first joint portion, and the second joint portion.

* * * * *